United States Patent [19]

Hollis, Jr.

[11] Patent Number: 4,842,861
[45] Date of Patent: Jun. 27, 1989

[54] ARTIFICIAL MAPLE CONCENTRATE ATTRACTANT RODENT BAITS

[76] Inventor: John P. Hollis, Jr., 7146 Spring Ter., San Antonio, Tex. 78249

[21] Appl. No.: 198,864

[22] Filed: May 26, 1988

Related U.S. Application Data

[63] Continuation-in-part of Ser. No. 848,639, Jan. 16, 1984, abandoned, which is a continuation-in-part of Ser. No. 168,368, Jul. 10, 1980, abandoned.

[51] Int. Cl.⁴ ............................................ A01N 25/08
[52] U.S. Cl. .................................................... 424/410
[58] Field of Search ...................... 514/460; 424/410

[56] References Cited

U.S. PATENT DOCUMENTS

| | | | |
|---|---|---|---|
| 2,783,177 | 2/1957 | Link | 424/84 |
| 4,012,520 | 3/1977 | Youngdale | 424/84 |
| 4,140,778 | 2/1979 | Dreikorn | 424/84 |
| 4,156,714 | 5/1979 | Lechevin et al. | 424/410 |
| 4,581,378 | 4/1986 | Lazar et al. | 424/17 |

OTHER PUBLICATIONS

Chem. Abst. 71:100158(s) (1969)–Holcenberg et al.
General Information Concerning Patents–1985.

*Primary Examiner*—Douglas W. Robinson

[57] ABSTRACT

This application discloses rodenticide and rodent-attracting compositions containing sugar-free maple concentrate attractant and Warfarin-masking saccharine (sodium). The disclosed compositions have greatly improved acceptability to the rodents and have a long storage life.

4 Claims, No Drawings

ARTIFICIAL MAPLE CONCENTRATE ATTRACTANT RODENT BAITS

This application is a continuation-in-part of Ser. No. 848,639 filed Jan. 16, 1984, now abandoned, which is a continuation-in-part of Ser. No. 168,368, filed July 10, 1980, now abandoned.

| U.S. PATENT DOCUMENTS | | |
|---|---|---|
| 4140778 | 2/1979 | Dreikorn, B. A. |
| 4581378 | 4/1986 | Lazar, R. and Lira, E. P. |
| 2783177 | 2/1957 | Link, K. P. |
| 3105321 | 10/1963 | Link, K. P. |
| 3816610 | 5/1972 | Lusby, W. S. |
| 3822211 | 7/1974 | Morton, L. V. N. |
| 3689655 | 9/1972 | Rosenberg F. J. and Miller, J. G. |
| 3865931 | 2/1975 | Ware, Jr., J. E., et al |
| 4012520 | 3/1977 | Youngdale, G. A. |

Rodents—rats and mice—have been associated with man since his earliest developments in agriculture, habitation and accumulation of foodstuffs. Rats in particular consume and contaminate, with feces, urine and decomposing matter, large amounts of agricultural products and stored food. Rats and mice carry and spread within the environment several infectious agents which cause diseases in man and in the lower animals. Rodents are a major pest problem worlwide; their control is pursued primarily with dangerous chemicals toxic also to man and domestic animals.

The economics of rodent control have imposed constraints upon use of extremely toxic chemicals and expensive baits. Prior art has made use of unattractive, cheaply-formulated baits containing the active ingredient Warfarin, a multiple-feeding anticoagulant toxicant and a variety of similar rodenticides.

Attempts to increase attractiveness of a Warfarin bait with maple syrup and maple formulations with sugar as a masking agent for Warfarin in patent application Ser. No. 168,368 were rejected on the ground that maple was sugar and sugar had been patented as an attractant. Therefore a CIP to 168,368, accepted as patent application Ser. No. 848,639, was presented, although in improper fashion, involving the use of sugar-free maple concentrate with saccharine (sodium) as a masking agent. This application was rejected on the grounds that sweeteners including saccharine had been shown attractant in rodent baits, and on the basis of improper claims; the alleged merits of sugar-free artificial maple concentrate were not addressed. The purpose of this CIP to Ser. No. 848,639 is to put the issue of artificial maple concentrates as attractant and saccharine (sodium) as masking agent for rodenticides in proper form with claims that match an area of opportunity about them which is virgin to practice, patents or literature.

Various rodent baits have been formulated. Patents by Lusby and Link show the use of combinations of Warfarin, grains and sugar. Ware, et al. discloses the use of oats, corn and sugar in a rodent bait. The patent of Rosenberg and Miller demonstrated rodents becoming reluctant to eat amounts of a particular bait beyond a certain level of consumption. Morton presents the use of anise as an animal attractant. Youngdale introduced various pharmaceuticals, which produced infertility in male rodents when admixed with saccharine and sucrose and diluents ethanol, glycerol and sorbitol to provide orally acceptable preparations. Dreikorn made use of sweetening agents—honey, molasses, corn syrup with standard animal feed formulations to patent a new class of rodenticides.

Sequencing of components in powdered form inorder to distribute, expose and mask them for maximum effectiveness and attractiveness is state of art for a Warfarin bait, that is essential when an attractant is included. The first step is mixing of the Warfarin with cracked corn. The second step is addition and mixing of rolled oats in order to transfer and distribute the starch containing Warfarin evenly on both cracked corn and rolled oat surfaces. The third step involves masking the Warfarin with a coating of starch containing saccharine (sodium); alternatively, both Warfarin and saccharine can be mixed within the starch diluent before addition to the other constituents. The final step involves addition by spraying of the sugar-free maple concentrate in 2 pounds of water on the moving bait surfaces already coated with saccharine (sodium).

Introduction of saccharine (sodium) as a substitute for sugar in a bait would be expected to insure a longer shelf life for the bait by preventing buildup of microorganisms which metabolize sugar.

Commercial rodent baits are quite effective against a few rats or mice, but against numbers in the thousands, they are limited in killing effectiveness to a 30–60 percent range by mediocre levels of attractiveness. The principal advantage and indeed reason for invention of the sugar-free maple concentrate attractant and its addition to bait is to increase the kill percentage to more that 97 percent. Extensive prior testing and shown this level of killing efficiency for the complete bait.

Introduction of sugar-free maple concentrate as a bait attractant should be feasible with baits containing rodenticides of such characteristic taste or odor that they do not require masking. Likewise the use of maple concentrate as an attractant in bait not containing rodenticide or sweetener would be useful in prebaiting procedures to accustom rodents to taking the bait. Finally the use of sugar-free maple concentrate attractant with saccharine (sodium) sweetener as a masking agent for Warfarin would not only greatly enhance bait attractiveness but should be cost competitive and stable in storage. Rats apparently are attracted to the bait at 0.04 weight percent maple concentrate, a level at which people are unable to detect the odor.

The artificial sugar-free maple concentrate attractant for testing was formulated from the ingredients listed in Table 1. Proprietary maple concentrates also tested are listed in footnote "a" of Table 1.

The present invention derives from two points: the efficacy of sugar-free maple concentrate attractant at weight percents in the range of 0.04–0.08, and the efficacy of saccharine (sodium) as a masking agent for Warfarin at weight percents in the range of 0.05–0.01, in specific conjunction with the use of maple concentrate (Table 2). The Warfarin masking (sub-attractant) range for saccharine (sodium) is much below the weight percent attractant range, (0.1–3.0) in sodium saccharine presented in Lazar and Lira.

In the bait consumption tests to be discussed, all bait formulations containing sugar-free artificial maple concentrate were at weight percents of 0.04. Likewise, all bait formulations which contained saccharine (sodium) were at 0.05 weight percents of this ingredient.

Various formulations of the bait in Table 2 were tested against an abundant population of feral rats (*Rat-*

*tus norvegicus* Exleben) beneath the Kalmbach-Burkett Feed Manufacturing Plant Building on Tecumseh Street in North Baton Rouge, La. in 10 paired comparison tests from Dec. 10, 1982 to July 10, 1983.

Table 3 shows the data from 10 paired comparisons as the percent bait consumed for each formulation. Ingredients of each formulation are shown at the base of Table 3. All comparisons, with the superior formulation listed first, were statistically significant at the 5 percent level, therefore only means percent bait consumption values are shown. Measurements of the final test series of July 10, 1983 were made Sept. 25, 1983.

The purpose of these 10 tests was to find out the efficacy of sugar-free artificial maple concentrate for bait attractiveness and the efficacy of saccharine (sodium) as a masking agent for the bitter taste of Warfarin. Three different tests of Formulation 6 against Formulation 5 showed the attractiveness of maple concentrate when saccharine was also present to mask Warfarin. Three tests also of Formulation 2 against Formulation 1 showed the attractiveness of maple concentrate in the absence of both Warfarin and saccharine. Two tests of Formulation 2 against Formulation 3 also showed the attractiveness of maple concentrate over saccharine in the absence of Warfarin. Finally, two tests of Formulation 5 over Formulation 4 showed the attractiveness of saccharine over Warfarin; since Warfarin is hardly an attractant, Formulation 5 over Formulation 4 shows an effective masking of Warfarin by saccharine.

In an earlier test, reported in Patent application Ser. No. 168,368, omission of coffee tincture from artificial maple concentrate markedly lowered efficiency of the bait.

Storage life of the baits, without measurable deterioration has been in excess of four years at room temperatures.

TABLE 1

Formulation of Sugar-Free Artificial Maple Concentrate Attractant

| Ingredients[a] | Relative Amount |
|---|---|
| foenugreek tincture[b] | 5 |
| ethyl alcohol 95 percent | 2 |
| coffee tincture | 2.5 |
| angelica tincture | .3 |
| balsam peru | .06 |
| vanillin (4 hydroxy-3-methoxy-benzaldehyde) | .04 |
| ethyl oenanthate (mixture of amyl and ethyl caprates with ethyl and isoamyl alcohols butyrates and caprylates | .01 |
| ethyl vanillin (3-ethoxy-4-hydroxy benzaldehyde | .01 |
| benzoic acid | .04 |
| sorbic acid | .04 |

[a]Ingredients for testing were obtained by purchase and from Dr. Robert Novak of the Food Science Dept., Louisiana State University, Baton Rouge, La., and relative amounts used in the artificial maple concentrate mixture were based on the Food Science literature on flavorings. Proprietary artificial maple concentrates were mapleleine imitation maple flavor manufactured by Crescent Manufacturing Company, Seattle, WN, and McCormick imitation maple flavor manufactured by McCormick and Company, Baltimore, MD.
[b]foenugreek tincture, relative amounts of (foenugreek-solid extract) 1, (water) 3, (propylene glycol) 6. coffee tincture, relative amounts of (instant soluble coffee) 4.54, (water) 3, (ethyl alcohol, 95 percent) 1.38, (propylene glycol) 1, (benzoic acid) .04, (sorbic acid) .04, angelica tincture, relative amounts of (pulverized angelica root) 1, (ethyl alcohol, 95 percent) 7, (water) 2.

TABLE 2

Formulation of Warfarin Rodent Baits with sugar-free artificial maple concentrate and saccharine (sodium) as masking agent for Warfarin.

| Ingredients[a] | Relative Amounts in Bait |
|---|---|
| cracked corn | 43–48 |
| Warfarin concentrate .05% in cornstarch | 5 |
| cornstarch | 4.975 |
| Warfarin | .025 |
| rolled oats | 43–48 |
| saccharine (sodium) 24 gms. dil. up to 5 lbs. with cornstarch containing Warfarin, or | 5 |
| cornstarch without Warfarin | 4.95–4.9 |
| saccharine (sodium) | .05–0.1 |
| maple concentrate 18.2 gms. dil. up to 4 lbs. with water | 4 |
| water | 3.96–3.92 |
| maple concentrate | 0.04–0.08 |
| Total | 100 |

[a]Basic ingredients corn, 43–48, oats, 43–48, starch, 5–10, water, 4 were maintained in relative amounts when Warfarin, saccharine or maple concentrate were omitted.

TABLE 3

Bait consumption (percent) by rats from 20 throw sacks each containing 100 grams bait for each formulation[a].

| Date of Test | Formulations compared | | | |
|---|---|---|---|---|
| Dec. 10, 1982 | 2 | 1 | 2 | 1 |
| percent bait consumed | 60.5 | 10.3 | 54.0 | 1.8 |
| Jan. 23, 1983 | 2 | 1 | 2 | 3 |
| percent bait consumed | 1.5 | 0 | 16.0 | 4.5 |
| March 14, 1983 | 2 | 3 | 5 | 4 |
| percent bait consumed | 22.0 | 2.0 | 97.0 | 1.5 |
| May 20, 1983 | 5 | 4 | 6 | 5 |
| percent bait consumed | 76.0 | 2.8 | 99.0 | 17.0 |
| July 10, 1983 | 6 | 5 | 6 | 5 |
| percent bait consumed | 86.0 | 7.5 | 98.0 | 10.5 |

[a]Formulations
1 Basic ingredients (B1) corn, oats, starch, water
2 B1 with maple concentrate
3 B1 with saccharine
4 B1 with Warfarin
5 B1 with Warfarin, saccharine
6 B1 with Warfarin, saccharine, maple concentrate

I claim:

1. A sugar-free rodenticidal composition which comprises a rodenticidal amount of Warfarin, a rodenticidal masking amount of about 0.05 to 0.10 weight percent of the composition of saccharine (sodium) a rodent attracting amount of about 0.04 to 0.08 weight percent of the composition of sugar-free artificial maple cncentrate, about 43 to 48 weight percent of cracked corn and 43 to 48 weight percent of rolled oats and about 5 to 10 weight percent of cornstarch.

2. The sugar-free rodenticidal composition of claim 1 wherein the saccharine (sodium) is present in the rodenticide masking amount of about 0.05 weight percent of the compositions.

3. The sugar-free rodenticidal composition of claim 1 wherein the sugar-free artificial maple concentrate is present in the attractant amount of about 0.04 weight percent of the compositions.

4. A method of enhancing the effectiveness and consumption of a rodenticidal bait comprising incorporating into said bait an attractant effective amount of a sugar-free aritificial maple concentrate.

* * * * *

UNITED STATES PATENT AND TRADEMARK OFFICE
CERTIFICATE OF CORRECTION

PATENT NO. : 4,842,861
DATED : June 27, 1989
INVENTOR(S) : John P. Hollis, Jr.

It is certified that error appears in the above-identified patent and that said Letters Patent is hereby corrected as shown below:

Column 1, line 29: "worlwide" should read --worldwide--.

Column 2, line 31: "and" should read --had--.

Column 3, line 51: add parenthesis ")" after "caprylates".

Column 3, line 52: add parenthesis ")" after "benzaldehyde".

Column 4, line 47: "cncentrate" should read --concentrate--.

Column 4, line 62: "aritificial" should read --artificial--.

Signed and Sealed this

Twenty-sixth Day of December, 1989

Attest:

JEFFREY M. SAMUELS

Attesting Officer     Acting Commissioner of Patents and Trademarks